(12) United States Patent
Place

(10) Patent No.: US 9,513,300 B2
(45) Date of Patent: Dec. 6, 2016

(54) DETERMINATION OF SERUM ANTI-MULLERIAN HORMONE AS A DIAGNOSTIC TEST FOR SPAY IN COMPANION ANIMALS

(75) Inventor: Ned J. Place, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 1021 days.

(21) Appl. No.: 12/435,607

(22) Filed: May 5, 2009

(65) Prior Publication Data
US 2009/0275060 A1 Nov. 5, 2009

Related U.S. Application Data

(60) Provisional application No. 61/050,458, filed on May 5, 2008.

(51) Int. Cl.
*G01N 33/53* (2006.01)
*G01N 33/74* (2006.01)
*G01N 33/58* (2006.01)

(52) U.S. Cl.
CPC ............ *G01N 33/74* (2013.01); *G01N 33/581* (2013.01); *G01N 2333/495* (2013.01); *G01N 2333/575* (2013.01)

(58) Field of Classification Search
None
See application file for complete search history.

(56) References Cited

U.S. PATENT DOCUMENTS

| | | | | |
|---|---|---|---|---|
| 4,874,691 A | * | 10/1989 | Chandler | 435/7.92 |
| 7,897,350 B2 | * | 3/2011 | Groome | C07K 16/26 435/7.1 |
| 2006/0275850 A1 | * | 12/2006 | Groome | C07K 16/26 435/7.92 |
| 2015/0104452 A1 | * | 4/2015 | Ghayur | C07K 16/28 424/136.1 |

FOREIGN PATENT DOCUMENTS

| | | | | |
|---|---|---|---|---|
| EP | 2161579 | * | 8/2008 | |
| GB | 2204398 A | * | 11/1988 | G01N 33/54366 |
| WO | WO 2007/125317 | * | 11/2007 | |

OTHER PUBLICATIONS

Active MIS/AMH ELISA DSL-10-14400, May 1, 2006.*
Adam et al., 2000, "Photoperiod regulates growth, puberty and hypothalamic neuropeptide and receptor gene expression in female Siberian hamsters", Endocrinology 141 4349-4356.
Baarends et al., 1995, "Anti-Müllerian hormone and anti-müllerian hormone type II receptor messenger ribonucleic acid expression in rat ovaries during postnatal development, the estrous cycle, and gonadotropin-induced follicle growth", Endocrinology 136 4951-4962.
Balla et al., 2003, "Dynamics of Ovarian Development in the FORKO immature mouse: structural and functional implications for ovarian reserve." Biology of Reproduction 69 1281-1293.
Bath et al., 2003, "Depletion of ovarian reserve in young women after treatment for cancer in childhood: detection by anti-Müllerian hormone, inhibin B and ovarian ultrasound", Human Reproduction 18 2368-2374.
Crisosto et al., 2007, "Anti-Mullerian hormone levels in peripubertal daughters of women with polycystic ovary syndrome", Journal of Clinical Endocrinology and Metabolism, 92 2739-43.
Dodge & Badura, 2002, "5HT and 5HIAA dialysate levels within the arcuate nucleus of the hypothalamus: relationship with photoperiod-driven differences in serum prolactin and luteinizing hormone in the Siberian hamster", Brain Research 946 171-178.
Durlinger et al., 1999, "Control of primordial follicle recruitment by anti-Müllerian hormone in the mouse ovary", Endocrinology 140 5789-5796.
Durlinger et al., 2001, "Anti-Müllerian hormone attenuates the effects of FSH on follicle development in the mouse ovary", Endocrinology 142 4891-4899.
Durlinger et al., 2002, "Anti-Müllerian hormone inhibits initiation of primordial follicle growth in the mouse ovary", Endocrinology 143 1076-1084.
Durlinger et al., 2002, "Regulation of ovarian function: the role of anti-Müllerian hormone", Reproduction 124 601-609.
Ebling, 1994, "Photoperiodic differences during development in the dwarf hamsters Phodopus sungorus and Phodopus campbelli", General and Comparative Endocrinology 95 475-482.
Elvin et al., 1999, "Molecular characterization of the follicle defects in the growth differentiation factor 9-deficient ovary", Molecular Endocrinology 13 1018-1034.
Faddy & Gosden, 1996, "A model conforming the decline in follicle numbers to the age of menopause in women", Human Reproduction 11 1484-1486.
Fortune, 2003, "The early stages of follicular development: activation of primordial follicles and growth of preantral follicles", Animal Reproduction Science 78 135-163.
Hirobe et al., 1992, "Müllerian inhibiting substance messenger ribonucleic acid expression in granulosa and Sertoli cells coincides with their mitotic activity", Endocrinology 131 854-862.
Hirshfield, 1994, "Relationship between the supply of primordial follicles and the onset of follicular growth in rats", Biology of Reproduction 50 421-428.
Hudson et al., 1990, "An immunoassay to detect human mullerian inhibiting substance in males and females during normal development", Journal of Clinical Endocrinology and Metabolism 70 16-22.
Ingraham et al., 2000, "Autocrine and paracrine Müllerian inhibiting substance hormone signaling in reproduction", Recent Progress in Hormone Research 55 53-67.
Ikeda et al., 2002, "Increased expression of Müllerian-inhibiting substance correlates with inhibition of follicular growth in the developing ovary of rats treated with E2 benzoate", Endocrinology 143 304-312.

(Continued)

*Primary Examiner* — Chris L Chin
(74) *Attorney, Agent, or Firm* — Casimir Jones, S.C.

(57) ABSTRACT

This invention relates to non-surgical assays that can be used to determine whether an animal that has a non-postpartum anestrous period of three months or greater, such as a dog or a cat, has been spayed. In particular, the present invention relates to devices, kits and methods that allow correlation of levels of Anti-Müllerian Hormone with the state of being spayed.

2 Claims, 4 Drawing Sheets

(56) References Cited

OTHER PUBLICATIONS

Jost, 1947, "Recherches sur la differenciation sexuelle de l'embryon de lapin", Archives d'anatomie microscopique et de morphologie expérimentale 36 217-315.

Kenny et al., 2002, "Photoperiod-dependent regulation of inhibin in Siberian hamsters: I. Ovarian inhibin production and secretion", Journal of Endocrinology 174 71-83.

Kenny et al., 2002, "Photoperiod-dependent regulation of inhibin in Siberian hamsters: II. Regulation of inhibin production and secretion by pregnant mare serum gonadotropin", Journal of Endocrinology 174 85-94.

Kevenaar et al., 2006, "Serum AMH levels reflect the size of the primordial follicle pool in mice", Endocrinology 147 3228-3234.

Knight & Glister, 2006, "TGF-beta superfamily members and ovarian follicle development", Reproduction 132 191-206.

Lee & Donahoe, 1993, "Mullerian inhibiting substance: a gonadal hormone with multiple functions", Endocrine Reviews 14 152-64.

Liao et al., 2000, "Direct reprobing with anti-actin as an internal control for western blot analysis", Biotechniques 28 216-218.

Moffatt-Blue et al., 2006, "Short photoperiod-induced ovarian regression is mediated by apoptosis in Siberian hamsters (Phodopus sungorus)", Reproduction 131 771-782.

Pedersen & Peters, 1968, "Proposal for a classification of oocytes and follicles in the mouse ovary", Journal of Reproduction and Fertility 17 555-557.

Pellatt et al., 2007, "Granulosa cell production of anti-Müllerian hormone is increased in polycystic ovaries", Journal of Clinical Endocrinology and Metabolism 92 240-255.

Place et al., 2004, "Short day lengths delay reproductive aging", Biology of Reproduction 71 987-992.

Scotti et al., 2007, "Short-day increases in aggression are independent of circulating gonadal steroids in female Siberian hamsters (Phodopus sungorus)", Hormones and Behavior 52 183-190.

Sir-Petermann et al., 2006, "Increased anti-Mullerian hormone serum concentrations in prepubertal daughters of women with polycystic ovary syndrome", Journal of Clinical Endocrinology and Metabolism 91 3105-9.

Timonin et al., 2006, "Phodopus campbelli detect reduced photoperiod during development but, unlike Phodopus sungorus, retain functional reproductive physiology", Reproduction 132 661-670.

Tremblay & Viger, 2001, "GATA factors differentially activate multiple gonadal promoters through conserved GATA regulatory elements", Endocrinology 142 977-986.

Ueno et al., 1989, "Müllerian inhibiting substance in the adult rat ovary during various stages of the estrous cycle", Endocrinology 125 1060-1066.

Van Den Hurk et al., 2002, "Enhanced serum oestrogen levels and highly steroidogenic, luteinized atretic follicles in the ovaries of the Djungarian hamster (Phodopus sungorus) kept under a short photoperiod from birth", European Journal of Endocrinology 147 701-710.

Van Rooij et al., 2005, "Serum antiMüllerian hormone levels best reflect the reproductive decline with age in normal women with proven fertility: a longitudinal study", Fertility and Sterility 83 979-987.

Visser et al., 2006, "Anti-Müllerian hormone: a new marker for ovarian function", Reproduction 131 1-9.

\* cited by examiner

DETERMINATION OF SERUM ANTI-MULLERIAN HORMONE AS A DIAGNOSTIC TEST FOR SPAY IN COMPANION ANIMALS

CROSS REFERENCE TO RELATED APPLICATIONS

This application claims the benefit of U.S. Provisional Application Ser. No. 61/050,458, filed May, 5, 2008, which is herein incorporated by reference in its entirety.

GOVERNMENT SUPPORT

This invention was made with government support under NIH-HD050358 awarded by the National Institute of Child Health and Human Development. The government has certain rights in the invention.

FIELD OF THE INVENTION

This invention relates to assays that can be used to determine whether an animal that has a non-postpartum anestrous period of greater than three months, such as a dog or a cat, has been spayed or neutered. In particular, the present invention relates to correlation of levels of Anti-Müllerian Hormone with the state of being spayed.

BACKGROUND OF THE INVENTION

The Humane Society of the United States estimates 6-8 million cats and dogs enter U.S. shelters annually, and approximately 58% of dogs and 46% of cats had not been spayed at the time they were relinquished. A definitive determination as to which animals are spayed or intact has become more difficult with evolving changes in practice, as a visible spay scar is often not apparent when animals are spayed at a very young age or when performed as a laparoscopic ovariectomy. Because the charters for most shelters require documented evidence that an animal has been spayed before they can be adopted out, many dogs and cats require exploratory surgery to determine their spay status. These procedures add costs to the already tight budgets of shelters, and expose many animals to potentially unnecessary surgery.

The presently available, non-surgical means by which presence or absence of the ovaries can be assessed are fraught with difficulties. As mentioned above, the spay scar has become less reliable, and some facilities may perform an exploratory laparatomy on all animals relinquished, because of missed diagnoses when an apparent spay scar was present. Vaginal cytology may be useful, but only if the animal presents during proestrus or estrus, and even then the testing may need to be supplemented by one or more determinations of serum estrogen or progesterone levels. Moreover, the measurement of sex steroids can yield equivocal results depending on the reproductive state of the animal, and more definitive tests that follow stimulation with an injection of gonadotropin releasing hormone (GnRH) are costly and require multiple visits and blood samplings. Similarly, a single measurement of luteinizing hormone (LH) was found not to be a reliable means for determining spay status, and as with sex steroids, GnRH stimulation has been recommended.

As such, a non-surgical diagnostic test is needed to reliably and affordably determine the spay status of shelter animals. Similarly, a better test is needed to assess suspected cases of the ovarian remnant syndrome, as the diagnostic tests presently available have substantial drawbacks. In particular, what is needed is a diagnostic test for a hormone or other factor that is easily and reliably detected in a single sample when the ovaries are present, or undetectable when the ovaries are completely absent.

SUMMARY OF THE INVENTION

This invention relates to assays that can be used to determine whether a companion animal such as dog or cat has been spayed or neutered. In particular, the present invention relates to correlation of levels of Anti-Müllerian Hormone (AMH) with the state of being spayed.

In some embodiments, the present invention provides non-surgical methods of determining whether a female animal that has a non-postpartum anestrous period or interestrous period of three months or greater has been spayed comprising: obtaining a sample from a female animal that has a non-postpartum anestrous period of three months or greater; assaying the sample for the level of Anti-Müllerian Hormone, wherein the level of Anti-Müllerian Hormone is correlated to the condition of being spayed or intact. In some embodiments, reduced levels of Anti-Müllerian Hormone as compared to a standard from an intact animal is indicative of a female animal that has a non-postpartum anestrous period or interestrous of three months or greater as being spayed. The present invention is not limited to any particular type of sample. In some embodiments, the sample is a serum sample. The present invention is not limited to any particular type of female animal that has a non-postpartum anestrous period or interestrous of three months or greater. In some embodiments, the female animal that has a non-postpartum anestrous period or interestrous of three months or greater is a companion animal. In some embodiments, the companion animal is selected from the group consisting of a dog and a cat. The present invention is not limited to the use of any particular type of assay device. In some embodiments, the presence of Anti-Müllerian Hormone is assayed by an assay device selected from the group consisting of an enzyme-linked immunosorbent assay, a lateral flow assay, and a flow through assay. The present invention is not limited to the use of any particular type of standard. In some embodiments, the standard is selected from the group consisting of a standard curve, a positive control from an intact animal, and a positive control from a spayed animal and combinations thereof.

In some embodiments, the present invention provides non-surgical method of determining whether a female animal that has a non-postpartum anestrous period or interestrous period of three months or greater has been spayed comprising: obtaining a sample from a female animal that has a non-postpartum anestrous period or interestrous of three months or greater and an antibody that binds the Anti-Müllerian Hormone; and contacting the sample with the antibody that binds to the Anti-Müllerian Hormone to determine the level of the Anti-Müllerian Hormone, wherein the level of Anti-Müllerian Hormone is correlated to the condition of being spayed or intact. In some embodiments, reduced levels of Anti-Müllerian Hormone as compared to a standard from an intact animal is indicative of a female animal that has a non-postpartum anestrous period or interestrous of three months or greater as being spayed. The present invention is not limited to any particular type of sample. In some embodiments, the sample is a serum sample. The present invention is not limited to any particular type of female animal that has a non-postpartum anestrous period of three months or greater. In some embodiments, the female animal that has a non-postpartum anestrous period or interestrous of three months or greater is a companion animal. In some embodiments, the companion animal is selected from the group consisting of a dog and a cat. The present invention is not limited to the use of any particular type of assay device. In some embodiments, the presence of Anti-Müllerian Hormone is assayed by an assay device selected from the group consisting of an enzyme-linked immunosorbent assay, a lateral flow assay, and a flow through assay. The present invention is not limited to the use of any particular type of standard. In some embodiments, the standard is selected from the group consisting of a standard curve, a positive control from an intact animal, and a positive control from a spayed animal and combinations thereof.

In some embodiments, the present invention provides kits for facilitating the non-surgical determination of whether a female animal that has a non-postpartum anestrous period or interestrous period of three months or greater has been spayed or neutered, comprising: an antibody that binds to Anti-Müllerian Hormone to form an antibody-Anti-Müllerian Hormone complex; a detection reagent that binds to the antibody-Anti-Müllerian Hormone complex to form a detection reagent-antibody-Anti-Müllerian Hormone complex; and a standard for comparison of the level of Anti-Müllerian Hormone in the female animal that has a non-postpartum anestrous period or interestrous of three months or greater so that the condition of being spayed can be determined. The present invention is not limited to any particular type of standard. In some embodiments, the standard is for a female animal selected from the group consisting of a dog and a cat. In some embodiments, the standard is selected from the group consisting of a standard curve, a positive control from an intact animal, and a positive control from a spayed animal and combinations thereof. The present invention is not limited to the use of any particular antibody. In some embodiments, the antibody that binds to Anti-Müllerian Hormone has been raised against cat or dog Anti-Müllerian Hormone. The present invention is not limited to the use of any particular type of detection reagent. In some embodiments, the detection reagent is a labeled antibody that binds to the Anti-Müllerian Hormone.

In some embodiments, the present invention provides devices for performing an assay to determine whether a cat or dog has been spayed comprising: a matrix that supports the flow of a liquid sample; an application zone on the matrix for receiving the liquid sample; one or more detection reagent zones on the matrix comprising detection reagents for conducting the assay; a detection zone on the matrix, the detection zone comprising an analyte binding area comprising a capture reagent specific for cat or dog Anti-Müllerian Hormone. The present invention is not limited to any particular capture reagent or detection reagent. In some embodiments, the capture reagent is an antibody specific for cat or dog Anti-Müllerian Hormone and the detection reagent is a labeled antibody specific for cat or dog Anti-Müllerian Hormone. The present invention is not limited to any particular assay format. In some embodiments, the detection zone further comprises a control zone.

DEFINITIONS

Figure 1:
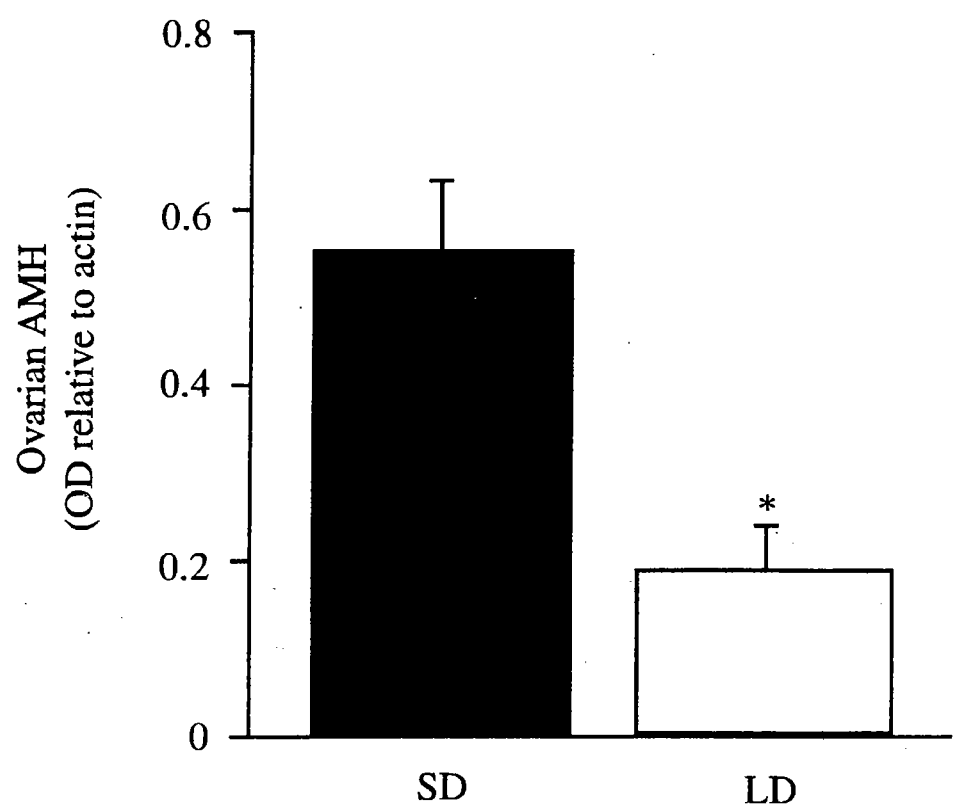
FIG. 1 provides a graph of mean (+SEM) serum AMH concentration (ng/ml) in female Siberian hamsters held in either short days (SD, 10 hours of light per day, filled bar) or long days (LD, 14 hours of light per day open bar) (n=7 for each group); * denotes significant effect of photoperiod.

To facilitate an understanding of the present invention, a number of terms and phrases are defined below:

The term "Anti-Müllerian Hormone" is abbreviated herein as AMH.

The term "AMH antibody" as used herein refers to an antibody that binds to AMH. In some embodiments, the AMH antibody is specific for cat or dog AMH.

The term "spay" as used herein refers to the removal of ovaries and/or uterus from an animal.

The term "spayed" as used herein refers to an animal from which the ovaries have been removed, and the uterus may or may not have been removed as well.

The term "intact" as used herein refers to an animal that possesses ovaries and/or a uterus.

The term "long day" is abbreviated herein as LD, and the term "short day" is abbreviated SD.

The term "long day (LD)" as used herein refers to a photoperiod of 14 to 16 hours of light per day, and the term "short day (SD) as used herein refers to a photoperiod of 10 hours of light per day.

The term "non-postpartum anestrous period" as used herein refers to a period where an animal does not exhibit a regular estrous cycle (e.g., a regular estrous period occurring every 2-6 weeks) other than the period encompassing pregnancy and subsequent lactation.

The term "interestrous period" as used herein refers to the interval between estrous periods.

The term "companion animal" as used herein refers to a domesticated animal that is typically kept for pleasure as a pet.

The terms "detecting" or "detection" or "determining the level" refer to quantitatively or non-quantitatively determining the presence of the analyte(s) under investigation (e.g., AMH). "Detecting Formation of a Complex" refers to detecting a complex comprising a detector reagent by any method suitable for observing the particular label associated with the detector reagent; for instance, visual observation of a colored (or otherwise visible) label, measurement or visual detection of a fluorescent, chemiluminescent or radioactive label.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include urine and blood products, such as plasma, serum and the like. Such examples are not however to be construed as limiting the sample types applicable to the present invention.

The term "specific binding partner (or binding partner)" refers to a member of a pair of molecules that interact by means of specific, noncovalent interactions that depend on the three-dimensional structures of the molecules involved. Typical pairs of specific binding partners include antigen/antibody, hapten/antibody, hormone/receptor, nucleic acid strand/complementary nucleic acid strand, substrate/enzyme, inhibitor/enzyme, carbohydrate/lectin, biotin/(strept) avidin, and virus/cellular receptor.

As used herein, the terms "immunoglobulin" or "antibody" refer to proteins that bind a specific antigen. Immunoglobulins include, but are not limited to, polyclonal, monoclonal, chimeric, and humanized antibodies, Fab fragments, F(ab')2 fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

The term "label" refers to a molecule or composition bound to an analyte, analyte analog, detector reagent, or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs. The attachment of a compound (e.g., a detector reagent) to a label can be through covalent bonds, adsorption processes, hydrophobic and/or electrostatic bonds, as in chelates and the like, or combinations of these bonds and interactions and/or may involve a linking group.

The phrase "specifically binds to an analyte" or "specifically immunoreactive with," when referring to an antibody, refers to a binding reaction which is determinative of the presence of the analyte in the presence of a heterogeneous population of molecules such as proteins and other biologic molecules. Thus, under designated immunoassay conditions, the specified antibodies bind to a particular analyte and do not bind in a significant amount to other analytes present in the sample. A variety of immunoassay formats may be used to select antibodies specifically immunoreactive with a particular analyte. For example, solid-phase ELISA immunoassays are routinely used to select monoclonal antibodies specifically immunoreactive with a protein. See Harlow and Lane, Antibodies, A Laboratory Manual, CSHP, New York (1988), for a description of immunoassay formats and conditions that can be used to determine specific immunoreactivity.

The term "capture agent" refers to an unlabeled specific binding partner that is specific for (i) an analyte, as in a sandwich assay, or (ii) a detector reagent or an analyte, as in a competitive assay, or for (iii) an ancillary specific binding partner, which itself is specific for the analyte, as in an indirect assay. As used herein, an "ancillary specific binding partner" is a specific binding partner that binds to the specific binding partner of an analyte. For example, an ancillary specific binding partner may include an antibody specific for another antibody, for example, goat anti-human antibody. A "capture area" is a region of a lateral flow device where the capture reagent is immobilized. A lateral flow device may have more than one capture area, for example, a "primary capture area," a "secondary capture area," and so on. Often a different capture reagent will be immobilized in the primary, secondary, or other capture areas. Multiple capture areas may have any orientation with respect to each other on the lateral flow substrate; for example, a primary capture area may be distal or proximal to a secondary (or other) capture area and vice versa. Alternatively, a primary capture area and a secondary (or other) capture area may be oriented perpendicularly to each other such that the two (or more) capture areas form a cross or a plus sign or other symbol.

The term "detector reagent" refers to a specific binding partner that is conjugated to a label. Detector reagents include, for example, labeled analyte-specific binding members or labeled ancillary specific binding members (such as enzyme-conjugate, goat anti-human antibodies).

The term "lateral flow device" refers to an analytical device in the form of a test strip used in lateral flow chromatography, in which a test sample fluid, suspected of containing an analyte, flows (for example by capillary action) through the strip (which is frequently made of bibulous materials such as paper, nitrocellulose, and cellulose). The test fluid and any suspended analyte can flow along the strip to a detection zone in which the analyte (if present) interacts with a detection agent to indicate a presence, absence and/or quantity of the analyte.

The term "sample application area" refers to an area where a fluid sample is introduced to a immunochromatographic test strip, such as an immunochromatographic test strip present in a lateral flow device. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

The term "solid support" or "substrate" means material which is insoluble, or can be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, microparticles (such as latex particles), and sheep (or other animal) red blood cells. Any suitable porous material with sufficient porosity to allow access by detector reagents and a suitable surface affinity to immobilize capture reagents is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

The surface of a solid support may be activated by chemical processes that cause covalent linkage of an agent (e.g., a capture reagent) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow substrate" is any solid support or substrate that is useful in a lateral flow device.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the terms "protein microarray" and "protein chip" refer to protein-detecting molecules immobilized at high density on a substrate, and probed for various biochemical activities. (See, for example: Zhu H and Snyder M, "Protein chip technology", Current Opinion in Chemical Biology 7: 55-63, 2003; Cutler P, "Protein arrays: The current state of the art", Proteomics 3; 3-18, 2003; and MacBeath G, "Protein microarrays and proteomics", Nature Genetics Supplement 32: 526-532, 2002, each of which is incorporated herein by reference in its entirety).

DESCRIPTION OF THE INVENTION

This invention relates to assays that can be used to determine whether female animals that have long non-postpartum anestrous periods, in particular companion animals such as dogs or cats, have been spayed or neutered. In particular, the present invention relates to correlation of levels of Anti-Müllerian Hormone (AMH) with the state of being spayed.

AMH, also known as Müllerian Inhibitory Substance (MIS), was first described as a hormone from the Sertoli cells within the developing testes that has an inhibitory effect on the development of the Müllerian (paramesonephric) ducts. The absence of AMH during early female sexual differentiation results in the development of oviducts, uterus, and upper vagina from the Müllerian ducts. However, ovarian follicles form during the perinatal period, and the granulosa cells that surround growing oocytes produce AMH throughout a female's reproductive life. As a result, AMH is found in the female circulation, and it has been measured in several mammalian species including our own. See, e.g., La Marca et al., J. Soc. Gynecol. Invest. 12(7):545-548. Because the serum concentration of AMH is a reasonable biomarker of ovarian follicular reserve, i.e., it correlates fairly well with the number of follicles remaining, AMH determinations are used in human infertility clinics to predict the likelihood of success for older women who may require in vitro fertilization.

The previous studies of AMH levels as related to number of follicles have been conducted in species, such as humans, mice, rats and cows, that have regular estrous periods and that do not have long non-postpartum anestrous periods. These animals with regular estrous periods can be expected to have baseline levels of AMH due to the constant recruitment of follicles for each successive estrous period. However, in animals that experience long anestrous periods, it is not expected that baseline levels of AMH, indicative of the presence of active ovaries, would be present because the ovaries are essentially inactive. Example 1 below presents a study of AMH levels in anestrous hamsters demonstrating several surprising findings. Specifically, animals with long anestrous periods do have baseline levels of AMH and these baseline levels, relative to estrous hamsters, was higher in the ovaries and lower in serum in anestrous hamsters. Thus, in contrast to animals with regular estrous periods, there appeared to be no correlation between AMH levels and the number of follicles or between AMH levels in the ovaries and AMH in serum. However, as shown in Example 2, baseline levels of AMH were detectable in dogs and cats, which also have long anestrous periods and this level of AMH was correlated with whether the animal was intact (i.e., had ovaries) or spayed (ovaries removed). In particular, spayed animals had low levels of AMH as compared to intact animals.

Accordingly, the present invention provides devices, kits and methods for determining whether a female animal, in particular female companion animals and animals with long non-postpartum anestrous periods or interestrous periods, have been spayed. In some embodiments, the long non-postpartum anestrous period is a non-postpartum anestrous period of 3 or more months, up to and including 9 months. In some embodiments, the interestrous period is a period of 3 or more months up to and including 9 months. These devices, kits and methods are used to determine AMH levels in an animal and then compare that level to a standard or control. Low levels of AMH as compared to the control or standard are indicative of the condition of being spayed. In some embodiments, the companion animal is a dog or cat. In some embodiments, the methods, kits and devices are used to assay the level of AMH in serum. In some embodiments, the level of AMH in a particular animal can be compared to a positive control or standard curve. A number of methods and devices can be used to assay AMH levels, including, but not limited to, enzyme-linked immunosorbent assay (ELISA) (such as the assays described below in detail and assays commercially available from Immunotech, Marseilles, France), Western blotting or protein detection chips.

A. Assay Devices and Methods

The present invention provides devices, kits and methods for detecting AMH in animals that have long non-postpartum anestrous periods, in particular to facilitate the determination of whether the animal has been spayed or is intact. The present invention is not limited to a particular detection assay. In some embodiments detection is, for example, fluorescent detection, spectrometric detection, chemiluminescent detection, matrix assisted laser desorption-time-of flight (MALDI-TOF) detection, high pressure liquid chromatographic detection, charge detection, mass detection, radio frequency detection, and light diffraction detection. Exemplary detection assays are described herein.

In some embodiments, of the present invention, AMH assays are suitable for point-of-care use such as at an animal shelter. In other embodiments, the assays are suitable for use in a clinical setting. In either embodiment, the AMH assays are used to determine the level of AMH in a test sample taken from a female animal having a long non-postpartum anestrous period. In some embodiments, the level of AMH in the test sample is compared to a standard, such as an AMH control sample or standard curve. In some embodiments, the standard is from an intact animal, while in other embodiments, the standard is from a spayed animal. In some embodiments, both types of standards are utilized. In some embodiments, a low level of AMH as compared to a standard derived from an intact animal is indicative of the condition of being spayed. In some embodiments, a level of AMH that is comparable to the standard derived from an intact animal is indicative of the condition of being intact. In some embodiments, a high level of AMH as compared to a standard derived from a spayed animal is indicative of the condition of being intact. In some embodiments, a level of AMH that is comparable to the standard derived from a spayed animal is indicative of the condition of being spayed.

In some embodiments, AMH is detected by binding of a capture molecule specific for the protein (for example, an aptamer, or an antibody in an immunoassay). The present invention is not limited to a particular capture molecule or antibody. Any capture molecule or antibody (e.g., monoclonal or polyclonal) that detects AMH may be utilized. Exemplary methods for the generation of antibodies are described below. Antibody-AMH complex resulting from antibody binding is detected by techniques known in the art. In some embodiments, a detection reagent is utilized. In some embodiments, the detection reagent is a labeled antibody that binds to AMH. The present invention is not limited to a particular detection format. A variety of detection formats are contemplated, including, but not limited to, radio-immunoassay, ELISA (enzyme linked immunosorbent assay), "sandwich" immunoassay, immunoradiometric assay, gel diffusion precipitation reaction, immunodiffusion assay, precipitation reaction, agglutination assay (e.g., gel agglutination assay, hemagglutination assay, etc.), complement fixation assay, immunofluorescence assay, protein A assay, and immunoelectrophoresis assay.

In some embodiments, assay devices, in particular ELISA devices, comprise coated microtiter plates. In some embodiments, a capture reagent (i.e., dog or cat AMH antibody) is applied in the wells of a microtiter plate. In this assay, a test sample (e.g., serum or blood) potentially containing an analyte of interest (e.g., AMH) is placed in the wells of a microtiter plate that contain the immobilized capture reagent. The analyte specifically binds the immobilized antibody; then, unbound materials are washed away leaving primarily the analyte-antibody complex bound to the plate. This complex can be detected in a variety of manners, such as by use of a labelled detector reagent, e.g., labeled dog or cat AMH antibody. One advantage of the microtiter plate format is that multiple samples can be tested simultaneously (together with controls) each in one or more different wells of the same plate; thus, permitting high-throughput analysis of numerous samples.

In some embodiments, a competitive ELISA assay is utilized (See e.g., U.S. Pat. Nos. 5,958,715, and 5,484,707, each of which is herein incorporated by reference). The competitive ELISA may be quantititative or non-quantitative. In a competitive ELISA, the wells of a microtiter plate are first coated with a fusion protein comprising all or a fragment of AMH. The sample to be tested is added to the plate along with an antibody that is specific for AMH. The AMH in the sample competes for binding to the antibody with the immobilized peptide. The plate is washed and the antibody bound to the immobilized AMH polypeptide is then detected using any suitable method (e.g., a secondary antibody comprising a label or a group reactive with an enzymatic detection system). The amount of signal is inversely proportional to the amount of AMH present in the sample (e.g., a high signal is indicative of low amounts of AMH being present in the sample).

In some embodiments, the immunoassay devices of the present invention permit the performance of relatively inexpensive, disposable, membrane-based assays for the visual identification of the presence (or absence) of an analyte in a liquid sample. Such devices are usually formatted as freestanding dipsticks (e.g., test strips) or as devices having some sort of housing. Typically, an immunoassay device of the present invention can be used with as little as about 200 μl of liquid sample, and detection of an analyte in the sample can (but need not) be complete within 2-5 minutes. In preferred embodiments, no ancillary instrumentation is required to perform such tests, and such devices easily can be used in clinics, laboratories, field locations, and the home even by inexperienced persons.

Immunoassay devices have been developed for the routine identification or monitoring of physiological and pathological conditions (e.g., infectious diseases, pregnancy, cancer, endocrine disorders) using different biological samples (e.g., urine, serum, plasma, blood, saliva), and for analysis of environmental samples (e.g., natural fluids and industrial plant effluents) for instance for contamination. Many of these tests are based on the highly specific interactions between specific binding pairs. Examples of such binding pairs include antigen/antibody, hapten/antibody, lectin/carbohydrate, apoprotein/cofactor and biotin/(strept)avidin. Furthermore, many of these tests involve devices (e.g., solid phase, lateral flow test strips, flow-through tests) with one or more of the members of a binding pair attached to a mobile or immobile solid phase material such as latex beads, glass fibers, glass beads, cellulose strips or nitrocellulose membranes (U.S. Pat. Nos. 4,703,017; 4,743,560; 5,073,484).

In some embodiments, the ELISA is an immunochromatographic "sandwich" assay. In general, sandwich immunochromatographic procedures call for mixing the sample that may contain the analyte to be assayed, for example, AMH, with an antibody specific for AMH. The antibody, i.e., detector reagent, is mobile and typically is linked to a label or another signaling reagent, such as dyed latex, a colloidal metal sol, or a radioisotope. This mixture is then applied to a chromatographic medium containing a band or zone of immobilized antibodies that recognize AMH (i.e., the capture antibody or reagent). The chromatographic medium often is in the form of a strip that resembles a dipstick. When the complex of AMH and the detector reagent reaches the zone of the immobilized capture antibody on the chromatographic medium, binding occurs and the detector reagent complex is localized at the zone. This indicates the presence of the molecule to be assayed. This technique can be used to obtain quantitative or semi-quantitative results. Examples of sandwich immunoassays performed on test strips are described in U.S. Pat. Nos. 4,168, 146 and 4,366,241, each of which is incorporated herein by reference.

In other embodiments, the ELISA is a solid phase immunoassay device that provides sensitive detection of analytes in biological fluid samples. Solid phase immunoassay devices incorporate a solid support to which one member of a ligand-receptor pair, usually an antibody, antigen, or hapten, is bound. Common early forms of solid supports were plates, tubes, or beads of polystyrene, which were known from the fields of radioimmunoassay and enzyme immunoassay. More recently, a number of porous materials such as nylon, nitrocellulose, cellulose acetate, glass fibers, and other porous polymers have been employed as solid supports. In other common forms of membrane-based immunoassays, as typified by some home pregnancy and ovulation detection kits, a test strip (or dipstick) is "dipped" into a sample suspected of containing the subject analyte. Enzyme-labeled detector reagent is then added, either simultaneously or after an incubation period. The device next is washed and then inserted into a second solution containing a substrate for the enzyme. The enzyme label, if present, interacts with the substrate, causing the formation of colored products, which either deposit as a precipitate onto the solid phase or produce a visible color change in the substrate solution. EP-A 0 125 118 describes such a sandwich type dipstick immunoassay. EP-A 0 282 192 describes a dipstick device for use in competition type assays.

In other embodiments, the assay device of the present invention is a flow through immunoassay device. Flow-through immunoassay devices involve a capture reagent (such as AMH antibody) bound to a porous membrane or filter to which a liquid sample is added. As the liquid flows through the membrane, target analyte (such as AMH) binds to the capture reagent. The addition of sample is followed by (or made concurrent with) addition of detector reagent (such as, labelled AMH antibody, labeled (e.g., gold-conjugated) Protein A or labeled (e.g., gold-conjugated) anti-AMH antibody IgG). Alternatively, the detector reagent may be placed on the membrane in a manner that permits the detector to mix with the sample and thereby label the analyte. The visual detection of detector reagent provides an indication of the presence of target analyte in the sample. Representative flow-through immunoassay devices are described in U.S. Pat. Nos. 4,246,339; 4,277,560; 4,632,901; 4,812,293; 4,920,046; and 5,279,935; and U.S. Patent Application Publication Nos. 20030049857 and 20040241876, all of which are incorporated by reference in their entirety. In some embodiments, the assay device is a migration assay device. Such devices usually incorporate within them reagents that have been attached to colored labels, thereby permitting visible detection of the assay results without addition of further substances. See, for example, U.S. Pat. No. 4,770, 853; PCT Publication No. WO 88/08534 and European Patent No. EP-A 0 299 428, all of which are incorporated by reference in their entirety.

In some embodiments, the assay device is lateral flow assay device. There are a number of commercially available lateral flow type tests and patents disclosing methods for the detection of analytes. See, e.g., U.S. Pat. Nos. 5,229,073; 5,591,645; 4,168,146; 4,366,241; 4,855,240; 4,861,711; 4,703,017; 5,451,504; 5,451,507; 5,798,273; 6,001,658; and 5,120,643; European Patent No. 0296724; WO 97/06439; and WO 98/36278, all of which are incorporated herein by reference.

The lateral flow assay devices of the present invention include a strip of absorbent or porous material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, AMH. Thus these zones can be viewed as functional sectors or functional regions within the test device.

In some embodiments, a fluid sample (or a sample suspended in a fluid) is introduced to the strip at the proximal end of the strip, for instance by dipping or spotting. A sample is collected or obtained using methods well known to those skilled in the art. The sample containing the AMH to be detected may be obtained from any biological source. Examples of biological sources include blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended or otherwise manipulated prior to immunoassay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

In some embodiments, the assay devices include a detector reagent. The detector reagent provides a means to detect the formation of a complex between an analyte (such AMH) and a capture reagent (such as a first AMH antibody). A detector may be integrated into an immunoassay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte. In other instances, a detector reagent collectively includes an unlabeled first binding partner specific for the analyte and a labeled second binding partner specific for the first binding partner and so forth. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

The flow-through devices of the present invention comprise a capture reagent (e.g., cat or dog AMH antibody) immobilized on a solid support such as a microtiter plate or a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize non-specific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (e.g., AMH) can specifically bind to the immobilized capture reagent (e.g., cat or dog AMH antibody). Where detection of an analyte-capture reagent complex is desired, a detector reagent (e.g., labeled Protein A, labeled AMH antibody) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

A lateral flow device is an analytical device comprising a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte. Many lateral flow devices are one-step lateral flow assays in which a biological fluid is placed in a sample area on a bibulous strip (though, non-bibulous materials can be used, and rendered bibulous, e.g., by applying a surfactant to the material), and allowed to migrate along the strip until the liquid comes into contact with a specific binding partner that interacts with an analyte in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

The construction and design of lateral flow devices is described, for example, in Millipore Corporation, A Short Guide Developing Immunochromatographic Test Strips, 2nd Edition, pp. 1-40, 1999, available by request at (800) 645-5476; and Schleicher & Schuell, Easy to Work with Bio-Science, Products and Protocols 2003, pp. 73-98, 2003, available by request at Schleicher & Schuell BioScience, Inc., 10 Optical Avenue, Keene, N.H. 03431, (603) 352-3810; both of which are incorporated herein by reference. Lateral flow devices have a wide variety of physical formats. Any physical format that supports and/or houses the basic components of a lateral flow device in the proper function relationship is contemplated by this disclosure.

In some embodiments, lateral flow devices of the present invention comprise an elongated housing containing a bibulous lateral flow strip that extends substantially the entire length of housing. In some embodiments, the lateral flow strip is divided into a proximal sample application pad positioned below a sample introduction port, an intermediate test result membrane, and a distal absorbent pad. The flow strip is interrupted by a conjugate pad that contains labeled conjugate (such labeled AMH antibody). A flow path along the strip passes from the proximal pad, through conjugate pad, into a test result membrane, for eventual collection in absorbent pad. Selective binding agents (such as cat or dog AMH antibody) are positioned on a proximal test line in the test result membrane. A control line is provided in the test result membrane slightly distal to the test line. A fluid sample containing an analyte of interest, such as AMH, is applied to the sample pad through the sample introduction port. In some embodiments, the sample may be applied to the sample introduction port dropwise or by dipping the end of the device containing the sample introduction port into the sample. From the sample pad, the sample passes, for instance by capillary action, to the conjugate pad. In the conjugate pad, the analyte of interest may bind (or be bound by) a mobilized or mobilizable detector reagent. For example, an AMH may bind to a labeled (e.g., gold-conjugated) AMH antibody detector reagent contained in the conjugate pad. The analyte complexed with the detector reagent may subsequently flow to the test result membrane where the complex may further interact with a capture reagent, such as AMH antibody, which is immobilized at the proximal test line. The formation of the immunocomplex between AMH, labeled (e.g., gold-conjugated) detector reagent, and immobilized AMH antibody can be detected by the appearance of a visible line at the proximal test line, which results from the accumulation of the label (e.g., gold) in the localized region of the proximal test line. The control line may contain an immobilized, detector-reagent-specific binding partner, which can bind the detector reagent in the presence or absence of the analyte. Such binding at the control line indicates proper performance of the test, even in the absence of the analyte of interest.

The particular materials used in a particular lateral flow device will depend on a number of variables, including, for example, the analyte to be detected, the sample volume, the desired flow rate and others. In some embodiments, the sample pad receives the sample, and may serve to remove particulates from the sample. In some embodiments, the sample pad is cellulose. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

The conjugate pad holds a detector reagent. In some embodiments, a detector reagent may be applied externally, for example, from a developer bottle, in which case a lateral flow device need not contain a conjugate pad (see, for example, U.S. Pat. No. 4,740,468). Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose.

The absorbent pad acts to increase the total volume of sample that enters the device. This increased volume can be useful, for example, to wash away unbound analyte from the membrane. Any of a variety of materials is useful to prepare an absorbent pad. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the level of AMH in serum is utilized. In other embodiments, the immunoassay described in U.S. Pat. Nos. 5,789,261, 5,599,677 and 5,672,480, each of which is herein incorporated by reference, is utilized.

In still other embodiments, a protein microarray or protein chip array assay is utilized for detection (See e.g., U.S. Pat. No. 6,197,599, herein incorporated by reference). In such an assay, proteins (e.g., antibodies specific for AMH) are immobilized on a solid support such as a chip. A sample suspected of containing AMH is passed over the solid support. Bound AMH is then detected using any suitable method. In some embodiments, detection is via surface plasmon resonance (SPR) (See e.g., WO 90/05305, herein incorporated by reference). In SPR, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical or chemical substance. The organic film contains antibodies (e.g., specific for AMH), which can bind with an analyte (e.g., AMH) in a sample to cause an increased thickness, which shifts the SPR angle. By either monitoring the position of the SPR angle, or the reflectivity at a fixed angle near the SPR angle, the presence or absence of an analyte in the sample can be detected.

In other embodiments, The PROTEINCHIP (Ciphergen Biosystems, Fremont, Calif.) is utilized for detection. The PROTEINCHIP system uses SELDI (Surface-Enhanced Laser Desorption/Ionization) technology to perform the separation, detection and analysis of proteins at the femptomole level directly from biological samples (See e.g., U.S. Pat. No. 6,294,790 and U.S. Patent Application US20010014461A1, each of which is herein incorporated by reference. In the PROTEINCHIP technology, proteins of interest (e.g., AMH) are captured on the PROTEINCHIP Array (e.g., via a bound antibody) directly from the original source material. The chip is washed to remove undesired materials and bound proteins are detected using SELDI.

In some embodiments, a cytometric bead array assay is used (Quantum Plex kit, Bangs Laboratories; Cytometric Bead Array kit, BD Biosciences). These systems allow for multiple analyte detection with small volume samples. In other embodiments, a LUMINEX bead assay is used.

B. AMH and AMH Antibodies

The devices, kits and methods of the present invention, which are described in detail below, utilize antibodies that bind to AMH and other reagents so that the level of AMH in a sample can be determined. In some embodiments, the AMH is AMH from a companion animal or from an animal that has a long non-postpartum anestrous period. In some embodiments, the AMH is from a dog or a cat. The sequence of dog AMH is known and available at Genbank Accession No. AAV97596. In some embodiments, the antibodies used in the present invention are specific for cat or dog AMH or have been prepared by using cat or dog AMH.

In some embodiments, the devices, kits and methods of the present invention utilize antibodies that are raised against dog or cat AMH. Accordingly, the present invention provides antibodies that bind to cat AMH or dog AMH. An antibody of the present invention may be any monoclonal or polyclonal antibody raised against cat or dog AMH, as long as it can recognize the cat or dog AMH. Antibodies can be produced by using cat or dog AMH as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody producing cells, an individual animal whose antibody titer has been confirmed (e.g., a mouse) is selected, and 2 days to 5 days after the final immunization, its spleen or lymph node is harvested and antibody producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS 1, P3U1, SP2/0, AP 1 and the like. The proportion of the number of antibody producer cells (spleen cells) and the number of myeloma cells to be used is preferably about 1:1 to about 20:1. PEG (preferably PEG 1000 PEG 6000) is preferably added in a concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against cat or dog AMH). For example, where a supernatant of the hybridoma is added to a solid phase (e.g., microplate) to which antibody is adsorbed directly or together with a carrier and then an anti immunoglobulin antibody (if mouse cells are used in cell fusion, anti mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM 101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti protein in the antiserum.

Separation and purification of a monoclonal antibody can be carried out according to the same manner as those of conventional polyclonal antibodies such as separation and purification of immunoglobulins, for example, salting out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared, and an animal is immunized by the complex according to the same manner as that described with respect to the above monoclonal antibody preparation. A material containing the antibody is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to a hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide-activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

In addition to polyclonal and monoclonal antibodies, any other antigen binding protein that binds to AMH, such as cat or dog AMH, may be utilized. Examples of other antigen binding proteins include chimeric and humanized antibodies, Fab fragments, F(ab')2 fragments, and single chain antibodies.

C. Kits

In some embodiments, the present invention provides kits for use in detecting AMH in a sample (such as, a biological sample). Such kits can be used, for example, to determine whether an animal having a long non-postpartum anestrous period has been spayed or is intact. Certain embodiments of the disclosed kits are generally portable and provide a simple, rapid, and/or cost-effective way to determine the presence or absence of AMH from animals having a long non-postpartum anestrous period without the need for laboratory facilities, such as in a point-of-care facility.

In some embodiments, the kits of the present invention include one or more immunoassay devices (and/or antigen-coated microtiter plates) as disclosed herein and a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control serum containing AMH), diluents (such as, phosphate buffers, or saline buffers), detector reagents (e.g., for external application to a kit device), substrate reagents for visualization of detector reagent enzymes (such as, 5-bromo-4-chloro-3-indolyl phosphate, nitroblue tetrazolium in dimethyl formamide), and/or wash solutions (such as, Tris buffers, saline buffer, or distilled water).

Other kit embodiments include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples into a sample chamber of an immunoassay device, including, for example, droppers, Dispo-pipettes, capillary tubes, rubber bulbs (e.g., for capillary tubes), and the like. Still other kit embodiments may include disposal means for discarding a used immunoassay device and/or other items used with the device (such as patient samples, etc.). Such disposal means can include, without limitation, containers that are capable of containing leakage from discarded materials, such as plastic, metal or other impermeable bags, boxes or containers.

In some embodiments, a kit of the present invention will include instructions for the use of an immunoassay device or antigen-coated plate. The instructions may provide direction on how to apply sample to the test device or plate, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify analyte using the test device, such as a standard curve relating intensity of signal or number of signal lines to an amount of analyte therefore present in the sample.

EXPERIMENTAL

Example 1

The mammalian ovary is endowed with a limited number of germ cells, and at any given point in a female's lifetime the number of primordial follicles represents the resting pool of oocytes from which she can draw upon for future reproductive efforts (Hirshfeld 1994). Continuous activation, or recruitment, of primordial follicles over time results in their numerical decline with age, and in women, menopause ensues when near or complete exhaustion of ovarian follicles occurs (Faddy & Gosden 1994). Several hormones and factors have been shown to modulate primordial follicle activation and most of these have been found to be stimulatory (reviewed in Fortune 2003). Conversely, there is convincing evidence that anti-Müllerian hormone (AMH, also known as Müllerian inhibiting substance or MIS) suppresses primordial follicle activation via autocrine and paracrine effects (Durlinger et al. 1999, 2002a). Until relatively recently, AMH was best known for its expression in Sertoli cells of developing testes and the regression of the Müllerian ducts in males during sexual differentiation (Jost 1947). However, differentiated ovaries also produce AMH and the granulosa cells of growing preantral follicles appear to be the principal source (Ueno et al. 1989, Hirobe et al. 1992, Baarends et al. 1995, Durlinger et al., 2002a, 2002b).

In female Siberian hamsters (*Phodopus sungorus*), short day (SD) conditions profoundly inhibit reproductive physiology and development (Ebling 1994, Adam et al. 2000), and the number of ovarian primordial follicles appears to be influenced by the photoperiod in which females are reared (Place et al. 2004, Timonin et al. 2006). Because AMH suppresses primordial follicle activation, we investigated the effects of day length on ovarian AMH expression in Siberian hamsters. Ovaries from females held in SD have an unusual feature—granulosa cells from preantral follicles appear to luteinize following atresia of the oocyte (van den Hurk et al. 2002, Place et al. 2004, Timonin et al. 2006) and the histology of these luteinized granulosa cells is consistent with continued steroidogenic activity (van den Hurk et al. 2002, Place et al. 2004). To determine if these granulosa cells continue to express AMH after oocyte atresia, we performed immunohistochemistry on ovaries from hamsters raised in either SD or long days (LD). Luteinized granulosa cells of atretic follicles within SD ovaries were immunoreactive for AMH, and because these cells account for a substantial portion of the SD ovary's volume, we predicted AMH protein expression would be greater in whole ovaries from SD as compared to LD hamsters.

Circulating levels of AMH decline with age, which may reflect the age-associated depletion of ovarian follicles (Kevenaar et al. 2006). Interestingly, serum AMH concentrations correlate with the number of ovarian primordial follicles in mice (Kevenaar et al. 2006) and women (Bath et al. 2003). Measurement of serum AMH concentration may be a useful marker when assessing a woman's probability of success when considering assisted reproductive technologies that require gonadotropin stimulation and collection of preovulatory oocytes (e.g., in vitro fertilization) (van Rooij et al. 2005). The number of primordial follicles within ovaries from Siberian hamsters raised in SD was approximately twice the number seen in age-matched LD ovaries (Place et al. 2004, Timonin et al. 2006), thus we measured serum AMH concentrations to test our prediction that circulating AMH would be higher in SD than LD hamsters.

Methods and Materials

Experimental Animals

Siberian hamsters from our colony (14 hours of light per day, 14L) were transferred to LD (16L) or SD (10L) as breeding pairs to generate females for this study. The time of lights-off was synchronized for all animals to 1700 Eastern Standard Time (EST). Animals were originally derived from wild-bred stock obtained from Dr. K. Wynne-Edwards, Queen's University. Experimental females were weaned on postnatal day 18, placed in polypropylene cages (2 to 4 siblings/cage), and maintained in the photoperiod in which they were born. Food (Teklad 8626, Madison, Wis.) and water were available ad libitum. Ambient temperature and relative humidity were held constant between $21° C.±5$ and $50±10\%$, respectively.

Blood and Tissue Collection

Fourteen LD and 14 SD females were given an intraperitoneal overdose of sodium pentobarbital, weighed, and then exsanguinated by retro-orbital bleed at 10 weeks of age. All animals were euthanized during the middle of the light cycle, between 1200 and 1400 EST. Blood was clotted on ice for at least 1 hr and centrifuged at 3,600 rpm for 20 min at 4° C. Drawn off serum was frozen and maintained at −80° C. until assayed for AMH.

Both ovaries were removed from each animal, dissected free of surrounding fat, and weighed on an analytical balance. One of the ovaries, selected pseudo-randomly from the right or left side, was placed in protein extraction buffer (10 mM Tris, 0.5M NaCl, 1 mM $MgCl_2$, 0.1% Triton X100, 1 tablet/10 ml Complete Mini Protease Inhibitor [Roche, Indianapolis, Ind.]) in preparation for Western blots. The remaining ovary from six animals in each group was immersed in 10% buffered formalin for histology and follicle counts, and half of those ovaries, three from each group, were used for AMH immunohistochemistry. Formalin fixation continued overnight at room temperature, followed by serial dehydration into 70% ethanol. Ovaries were embedded in paraffin and serially sectioned at 6 μm. Every tenth section was stained with hematoxylin and eosin and viewed under 400× magnification to count the types of ovarian follicles that express AMH with the greatest intensity, i.e., primary and secondary follicles. Because AMH is principally expressed in granulosa cells, we further subdivided secondary follicles into categories with less than 4 layers of granulosa cells (types 4 and 5a), or 4 or more layers of granulosa cells (type 5b) surrounding the oocyte (Pedersen & Peters 1968). Primary follicles were defined as an oocyte surrounded by a single layer of cuboidal granulosa cells.

Immunohistochemistry for AMH

Six mid-ovary sections from each of three animals in each group were immunostained for AMH. Sections from LD and SD ovaries were alternately placed on each slide to control for potential staining variability between slides. Adjacent sections were mounted on separate slides for negative controls. After dewaxing and rehydration in a series of ethanols, endogenous peroxides were quenched in hydrogen peroxide (0.3% in methanol) for 30 min. Sections were then incubated in 10% normal rabbit serum diluted in dilution buffer (0.5M Sodium chloride, 0.01M Phosphate Buffer, 3% BSA, 0.3% Triton-X 100) for 20 min at room temperature to block nonspecific binding sites. Polyclonal goat anti-MIS antibody (sc-6886, Santa Cruz Biotechnology, Santa Cruz, Calif.) was diluted 1:1000 in dilution buffer and incubated with sections for 16 hours at 4° C. As a negative control, primary antibody was incubated 1:1 overnight with MIS (C-20) Blocking Peptide (sc-6886P, Santa Cruz Biotechnology, Santa Cruz, Calif.) on a rocker at 4° C. before its application to sections as described above. Additional negative controls excluded the primary or secondary antibody. Sections were incubated with the secondary antibody, biotinylated rabbit anti-goat IgG (Santa Cruz Biotechnology; 1:200 in dilution buffer), for 30 min. Immunoreactivities were visualized by incubating sections with Vectastain Elite ABC Solution (Vector, Burlingame, Calif.) for 30 min and developed with NovaRed Peroxidase Substrate Solution (Vector, Burlingame, Calif.) following the manufacturer's instructions. Sections were counterstained with hematoxylin.

Western Blot for AMH

Freshly collected ovaries were homogenized in protein extraction buffer, and protein concentrations were determined with the DC Protein Assay Kit (Bio-Rad, Hercules, Calif.). For each sample, approximately 10 μg of protein were resolved on a 10% SDS gel under reducing conditions, followed by transfer onto a nitrocellulose membrane (Bio-Rad, Hercules, Calif.). The membrane was incubated in SuperBlock Blocking Buffer in TBS (Pierce, Rockford, Ill.) for 60 min at room temperature to block nonspecific binding sites. Polyclonal goat anti-MIS antibody (sc-6886, Santa Cruz Biotechnology, Santa Cruz, Calif.) was diluted 1:1000 in SuperBlock Blocking Buffer and incubated overnight at 4° C. on a rocker. Specific binding was detected using horse peroxidase anti-goat secondary antibody (PI-9500, Vector, Burlingame, Calif.) at a dilution of 1:50,000. Labeled proteins were visualized by SuperSignal West Pico Chemiluminescents Substrate (Pierce, Rockford, Ill.) and viewed by autoradiography. Using the direct reprobing method outlined in Liao et al. (2000), the relative intensity of AMH was determined using β-actin as the loading control. Briefly, the blot was incubated for 1 hr at room temperature with monoclonal mouse anti-β-actin (Clone AC-150; Sigma, St. Louis, Mo.) diluted 1:5000 in SuperBlock Blocking Buffer, then probed for 1 hr at room temperature with goat peroxidase anti-mouse secondary antibody (31430, Pierce, Rockford, Ill.) at a dilution of 1:100,000. Labeled proteins were visualized as stated above.

Western blot films were scanned into a MacIntosh computer and the optical density of AMH and β-actin were analyzed with imaging processing software (ImageJ 1.34s, NIH, Bethesda, Md.). AMH immunoreactivity was expressed relative to β-actin for each ovary.

ELISA for AMH

AMH was measured in duplicate serum samples using an enzyme-linked immunosorbent assay (ELISA) produced by Diagnostic Systems Laboratories (Webster, Tex.). This ELISA was validated for the measurement of AMH in Siberian hamsters by serially diluting a hamster serum sample in the kit's sample diluent and demonstrating parallelism with the standard curve (range 0.05 to 15 ng/ml). The undiluted sample had a starting concentration of 4.26 ng/ml. All samples were run in a single assay and the intra-assay coefficient of variation was 22.0%. The minimum detection limit of the assay as reported by the manufacturer was 0.006 ng/ml.

Statistical Analysis

Results were analyzed with a commercial statistical program (JMP version 5.1.2, SAS Institute, Cary, N.C.). LD v. SD comparisons of body and paired ovarian mass were made with t-tests, as were comparisons of ovarian and serum AMH. Uterine mass data were not normally distributed and the LD and SD variances were statistically different, thus the Median test was used for the uterine mass comparison. Because our preliminary data included animals from the same litter, we averaged all data from females within the same litter and treated the mean as a single data point. Thus, sample sizes reflect the number of litters represented, and litters in both groups contained from one to five females. We repeated all analyses using values from all individuals, and the statistical findings were identical to litter-based analyses. Pearson product-moment was used to determine if serum AMH concentration (by ELISA) correlated with ovarian AMH expression (by Western blot). Differences at $p<0.05$ were considered to be significant.

Results

Body, Uterine, and Paired Ovarian Mass

When animals were killed at 10 weeks of age, females held in LD weighed significantly more than SD females. Uterine mass and paired ovarian mass were also greater in LD than in SD females (Table 1). Based on body, uterine, and paired ovarian mass, none of the SD females appeared to be photononresponders.

TABLE 1

Body, uterine, and paired ovarian mass in Siberian hamsters reared in long or short days

|  | Long Day (n = 7) | Short day (n = 7) | P value |
|---|---|---|---|
| Body mass (g) | 29.8 ± 1.2 | 20.8 ± 1.2 | 0.002[a] |
| Uterine mass (mg) | 126.1 ± 26.2 | 15.0 ± 4.1 | <0.001[b] |
| Paired ovarian mass (mg) | 9.7 ± 0.4 | 6.4 ± 0.7 | 0.003[a] |

[a]Student's t-test
[b]Median test

Ovarian Histology and Immunohistochemistry

Ovarian histology was noticeably different in females raised in SD as compared to LD. Antral follicles were commonplace and corpora lutea (CL) were often present in LD, but not SD ovaries (Table 2; photomicrographs not shown). Follicle development rarely advanced beyond the secondary stage in SD ovaries, and the SD ovary was also characterized by an abundance of hypertrophied eosinophilic cells, which surround atretic oocytes (photomicrographs not shown).

TABLE 2

Ovarian follicle counts in Siberian hamsters reared in long or short days

| Day length | Primary | Secondary Types 4 and 5a | Type 5b | Antral | Corpora lutea[a] |
|---|---|---|---|---|---|
| Long (16L) | 25.2 ± 3.6 | 17.3 ± 2.1* | 6.8 ± 0.9 | 2.2 ± 0.5[b] | 3/6 |
| Short (10L) | 34.5 ± 4.5 | 8.2 ± 1.8 | 4.8 ± 1.5 | 0.3 ± 0.3[c] | 0/6 |

*Long day significantly greater than SD (P < 0.05)
[a]Number of females in each group that had at least one corpus luteum
[b]Five out of six LD females had at least one antral follicle
[c]Two out of six SD females had one antral follicle, the remaining four females had none Granulosa cells within primary and secondary follicles in both LD and SD ovaries showed the most intense staining for AMH following immunohistochemistry (photomicrographs not shown). AMH seemed to be less intense in the granulosa cells of antral follicles and absent in CL (photomicrographs not shown). AMH staining of moderate intensity was seen in the hypertrophied, or "luteinized", granulosa cells that surround atretic oocytes in SD ovaries (photomicrographs not shown), whereas the cells surrounding atretic oocytes in LD ovaries were neither luteinized nor positive for AMH (photomicrographs not shown). Pre-incubation of the antisera for AMH with blocking peptide before immunohistochemistry (photomicrographs not shown) confirmed the specificity of the AMH staining in the luteinized granulosa cells in SD ovaries. Non-specific AMH staining was not seen in negative controls, i.e., when the primary or secondary antibody was omitted, or when normal serum was used in substitution for the primary antibody (not shown). AMH immunohistochemistry of neonatal Siberian hamster testes revealed staining limited to Sertoli cells, as expected (not shown).

Because the most intense AMH staining was seen in primary and secondary follicles, we counted the numbers of these types of follicles and found greater numbers of small secondary follicles (types 4 and 5a) in LD as compared to SD ovaries, but no significant difference in the numbers of primary or large secondary (type 5b) follicles (Table 2).

Western Blots

Western blot for AMH protein showed a single band in both LD and SD ovaries at the expected size (~70 kDa) (Not shown). Whereas AMH expression was minimal to moderate in LD ovaries, AMH in SD ovaries was consistently moderate to high. Mean AMH protein level relative to β-actin expression was more than 3-fold higher in SD than in LD ovaries (data not shown). Because CLs can occupy a substantial volume of LD ovaries and do not express AMH, we tried to determine if the presence of CLs in the ovary, as determined by histology, predicted lower AMH expression by Western blot in the contralateral ovary. With small sample sizes (3 LD ovaries with CLs and 3 without), which limited statistical power, we could detect no clear association between presence or absence of CLs and AMH expression of the ovary as a whole.

Serum AMH ELISA

Despite higher AMH protein expression in the ovaries of SD females, serum AMH concentration was significantly lower in SD than in LD females (t=3.00; p=0.01) (FIG. 1). The correlation (r=−0.353) between ovarian and serum AMH was not significant (p=0.09). As with ovarian AMH, presence or absence of CLs in ovaries of LD females did not seem to overtly impact serum AMH concentration (LD with CL: 3.7±0.6 ng/ml, n=3; LD without CL: 3.4±0.4 ng/ml, n=3).

Discussion

Siberian hamsters raised in SD demonstrate a profound inhibition of somatic and reproductive development (Ebling 1994, Place et al. 2004, Timonin et al. 2006), and the ovarian morphology of SD females is proving to be very interesting. Because AMH has been shown to inhibit primordial follicle activation (Durlinger et al. 1999, 2002a) and SD female hamsters had significantly more primordial follicles than age-matched LD hamsters (Place et al. 2004), we postulated that ovarian AMH might be modulated by photoperiod. The three-fold higher AMH levels in SD as compared to LD ovaries is an attractive mechanistic candidate for the preservation of primordial follicles and deceleration of reproductive aging in female hamsters raised in SD. However, the findings of the present study represent correlation and not causation. Nevertheless, these initial results are a good starting point for elucidating the means by which day length influences the numbers of primordial follicles and reproductive aging in *P. sungorus* (Place et al. 2004).

Lower AMH concentration in the serum of SD as compared to LD females suggests the actions of AMH on primordial follicle activation may be paracrine or autocrine in nature, as proposed by others (Ingraham et al. 2000, Durlinger et al. 2002, Knight & Glister 2006). The disparity between ovarian and serum AMH levels in LD and SD hamsters may reflect the variation in their ovarian morphology. For example, differences in the vascularization of SD and LD ovaries may explain the discrepancy. Ovaries from 10 wk-old SD females weighed significantly less than LD ovaries (Timonin et al. 2006, present study, Table 1) and thus SD ovaries may be less vascular. In fact, granulosa cells within ovarian follicles form an avascular layer (Irving-Rodgers & Rodgers 2000) and the AMH-expressing hypertrophied granulosa cells, which account for much of the SD ovary's volume (data not shown), appear to be luteinized but lack the increased vascularity that characterizes corpora lutea. Female hamsters raised in SD had more primordial follicles than age-matched LD females (Place et al. 2004, Timonin et al. 2006), and because Kevenaar et al. (2006) found circulating AMH to correlate with the size of the primordial follicle pool in mice, we expected serum AMH to be higher in SD than in LD females. SD hamsters showed an advantage over LD females in primordial follicle numbers at 13 and 26 weeks of age (Place et al. 2004), and a preliminary determination of the serum AMH concentration in animals from that study revealed lower AMH in SD at 13 wk of age, but higher AMH in SD at 26 wk of age (unpublished). We have interpreted these results with caution because the serum samples used had undergone a thaw-refreeze-thaw cycle before AMH determination. Nevertheless, it appears the relationship between the primordial follicle reserves and circulating AMH concentration in Siberian hamsters may be more complex than in mice, and day length may be a modulating factor. Differences in reproductive state may also contribute to the lower serum AMH levels in SD as compared to LD hamsters. Some years ago, serum AMH was reported to be barely detectable or extremely low in prepubertal women (Hudson et al. 1990, Lee & Donahoe 1993), but these investigators used an ELISA with limited sensitivity (0.5 ng/ml). The sensitivity of newer ELISA's has improved (0.006 ng/ml) and a more recent study has reported appreciable levels of AMH in the serum of infants and young girls (Sir-Petermann et al. 2006). However, these same investigators measured higher levels in peripubertal girls (Crisosto et al. 2007), which suggests serum AMH is relatively low in females before puberty. Thus, lower serum AMH concentration in 10 wk-old SD hamsters may simply reflect their prepubertal state, but still, the underlying etiology remains unknown.

Because we found LD ovaries had a comparable or greater number of the follicle types that express AMH most intensely (types 4 and 5) as compared to SD ovaries (Table 2), we suspect the greater AMH expression seen in SD ovaries by Western blot probably reflects the contribution made by the AMH-expressing luteinized granulosa cells. Alternatively, AMH expression may be up-regulated in granulosa cells that are affiliated with healthy follicles in SD ovaries. Why granulosa cells in SD ovaries persist and luteinize whilst they surround an atretic oocyte remains to be determined. A similar phenotype has been seen in mice deficient in growth differentiation factor-9 (GDF9), in that granulosa cells within primary follicles luteinized when the oocyte underwent atresia (Elvin et al. 1999). Those investigators did not assess AMH expression in the luteinized granulosa cells from GDF9 deficient mice, but the luteinized cells were positive for some luteal markers (e.g., LH receptor and P-450 side chain cleavage [P450scc]) as well as nonluteal markers (e.g., inhibin α and P-450 aromatase [P450arom]). We did not detect AMH expression in the Siberian hamster CL (data not shown), which means the luteinized granulosa cells in SD ovaries express at least one nonluteal marker. In contrast to the GDF9 deficient mouse, Kenny et al. (2002a) reported the luteinized granulosa cells from Siberian hamsters held in SD probably do not express the inhibin α-subunit. However, their figures (in situ hybridization) do not provide the histological details necessary to clearly distinguish cell and follicle types. Nevertheless, Kenny et al. (2002a) found significantly lower levels of inhibin α-subunit in ovaries from SD versus LD females.

The intense eosinophilia of the luteinized granulosa cells within hamster SD ovaries suggests they are active in steroidogenesis, and van den Hurk et al. (2002) reported especially strong enzyme activity for 3α-hydroxysteroid dehydrogenase (3β-HSD) in what they referred to as "hypertrophied granulosa cells of luteinized atretic follicles". P450arom activity or expression has not been investigated in SD hamster ovaries, but van den Hurk et al. (2002) found serum estradiol (E2) concentration was significantly higher in SD than in LD female hamsters on postnatal days 28, 56, and 80. Whether luteinized granulosa cells account for the higher circulating E2 via P450arom activity remains to be determined. However, the higher serum E2 concentration reported for SD female hamsters (van den Hurk et al. 2002) seems paradoxical and warrants confirmation. The uterus, a highly estrogen sensitive organ, weighs significantly less in female hamsters raised in SD as compared to LD (Ebling 1994, Place et al. 2004, Timonin et al. 2006; present study—Table 1), and we have recently confirmed this finding (unpublished results) at all ages for which van den Hurk et al. (2002) reported significantly higher serum E2 levels in SD females. Moreover, Scotti et al. (2007) used the same commercial radioimmunoassay (RIA) kit as van den Hurk et al. (2002) to measure serum E2 in Siberian hamsters held in LD and SD, except Scotti et al. (2007) performed a diethyl ether extraction of steroids before proceeding with the RIA. Scotti et al. (2007) found no significant effect of photoperiod on serum E2 concentration, however their SD hamsters were adults that had been transferred from LD to SD, whereas van den Hurk et al. (2002) transferred hamsters from LD to SD at birth. Because E2 has been purported to both inhibit (Barrends et al. 1995, Balla et al. 2003) and stimulate (Ikeda et al. 2002) ovarian AMH expression, it will be important to determine if P450arom is expressed by luteinized granulosa cells and if hamsters raised in SD in fact have higher serum E2 concentrations than females reared in LD. Unfortunately, sample volume limitations precluded us from measuring serum E2 in the present study.

The circulating concentration of follicle stimulating hormone (FSH) is lower in female Siberian hamsters when raised in SD as compared to LD (Kenny et al. 2002a), and this may contribute to the differences in ovarian morphology and AMH expression. Bareends et al. (1995) noted a decrease in ovarian AMH expression following administration of human recombinant FSH to rats, and Balla et al. (2003) reported an up-regulation of AMH in ovarian granulosa cells in the follitropin receptor knockout (FORKO) mouse. Similar to SD hamsters, in which antral follicles are rare (present study) or absent (Place et al. 2004, Timonin et al. 2006), FORKO mice lack ovarian follicles that develop beyond the preantral stage. However, luteinized granulosa cells have not been reported in the ovaries of FORKO mice, and this may reflect differences in the hormonal milieu as compared to SD hamsters. Plasma LH was elevated in FORKO mice relative to wild-type and plasma estradiol was undetectable (Balla et al. 2003). Conversely, serum LH concentration has been reported to be much lower in SD than in LD female hamsters (Dodge & Badura, 2002), but E2 concentration does not appear to be consistently lower in SD as compared to LD hamsters (van den Hurk et al. 2002, Scotti et al. 2007; but see Moffatt-Blue et al. 2006). The similarities and differences in the ovarian phenotype of SD hamsters with that of GDF9 deficient and FORKO mice should help direct future investigations to determine the mechanisms/signals that underlie the luteinization of granulosa cells and the up-regulation of AMH in SD ovaries. Logical starting points will be to examine SD-ovary expression of GDF9 as well as GATA4, which mediates the inhibition of AMH via the FSH receptor (Tremblay & Viger 2001, Balla et al. 2003).

In addition to its inhibitory effects on primordial follicle activation (Durlinger et al. 1999, 2002a), AMH has also been shown to inhibit the growth of preantral and antral follicles in mice (Durlinger et al. 2001), by modulating the sensitivity of growing follicles to FSH (Visser et al. 2006). The higher AMH expression in SD hamster ovaries may explain the findings reported by Kenny et al. (2002b), whereby the ovarian response to an in vivo gonadotropin challenge (pregnant mare serum gonadotropin, PMSG) was blunted in juvenile SD hamsters relative to LD females. PMSG-induced follicular growth that was not as great in SD as compared to LD females, and SD females could not be induced to ovulate when an LH analog (human chorionic gonadotropin) was administered 48 h after PMSG. These results are intriguing in light of the recent report that AMH production by granulosa cells from women with polycystic ovary syndrome (PCOS) was significantly increased as compared to normal ovaries, and this may contribute to the anovulatory phenotype in PCOS (Pellatt et al. 2007).

In conclusion, the profound effect of photoperiod on reproductive function in female Siberian hamsters, and on their ovarian physiology in particular, suggests this species will be a valuable animal model for the study of ovarian follicle development. The activation of primordial follicles is still a poorly understood phenomenon, and the findings that SD rearing preserves the number of primordial follicles and enhances ovarian AMH expression in *Phodopus sungorus* adds further support for the critical role that AMH plays in follicular dynamics. Because we have the potential to dictate when juvenile SD females transition to the LD (mature) ovarian phenotype, simply by transferring them to a LD photoperiod, we may be able to better understand the conditions and signals in the ovary that modulate follicle activation and later stages of follicular development.

Example 2

Canine and feline serum samples that were referred to the Diagnostic Endocrinology Laboratory for routine testing were used in a study to measure AMH using an enzyme-linked immunosorbent assay (ELISA) from Diagnostic Systems Laboratories (DSL-10-14400). AMH analyses were delayed until all requested test results were finalized and reported. The residual volume of samples was stored frozen until assayed for AMH. Requisition forms were reviewed to identify an even mix of spayed and intact animals. No attempt was made to confirm the spay status of these cases, thus there was a risk that some animals may have been misidentified as spayed or intact. The most likely scenario would be failure to indicate that an animal had been spayed. Because serum AMH levels decline with age, and may be undetectable in post-reproductive aged females, the age of each animal was recorded if that information was included on the requisition form.

Figure 2A:
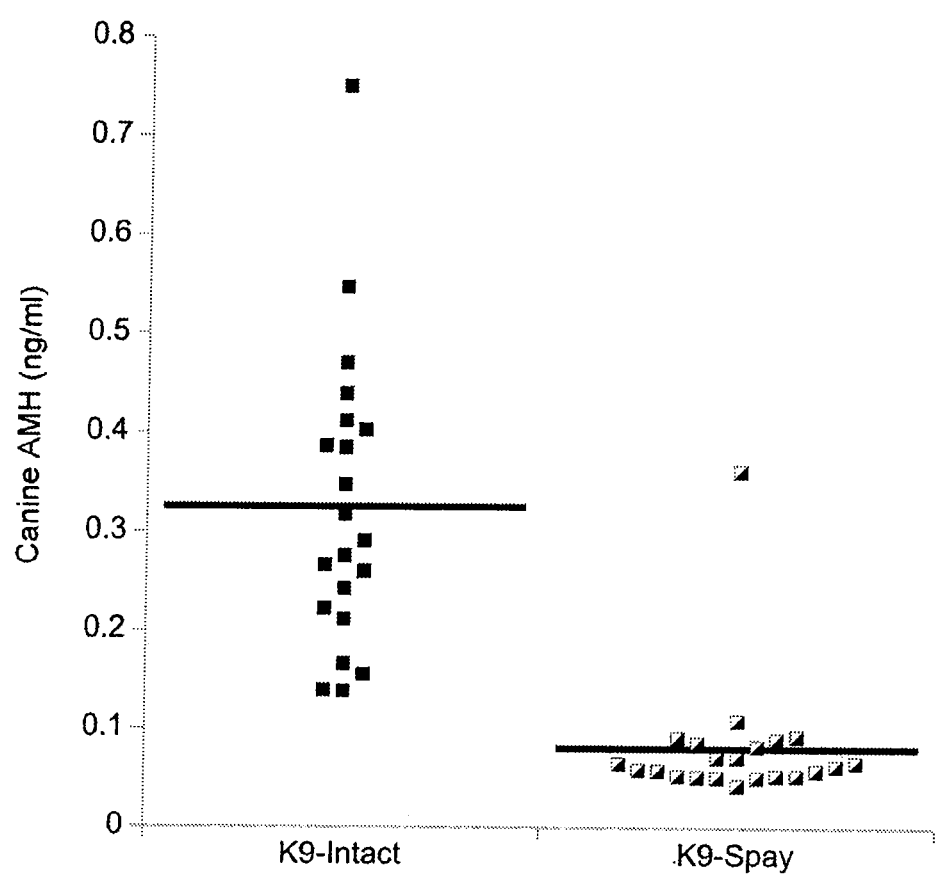
FIGS. 2 (A) and (B) are graphs of serum concentrations of AMH in (A) canine and (B) feline samples. Horizontal lines indicate means of each group. Group designations were determined by entries on lab requisition forms, thus spay/intact status may not be absolute.

A total of 54 canine (30 intact, 22 spay, 2 confirmed ovarian remnant) and 49 feline (24 intact, 25 spay) serum samples were assayed according to the manufacturer's instructions. For dogs, AMH concentration was nearly uniformly low in the spay group (FIG. 2A). The hospital records for the single outlier were reviewed and this animal was determined to be an old english sheepdog admitted with thyroid carcinoma and hyperparathyroidism, thus an ectopic source for AMH cannot be ruled out. Nor could we definitively determine if this dog had been in fact spayed. The AMH levels for two confirmed cases of ovarian remnant syndrome were well within the range of intact dogs (0.18 and 0.19 ng/ml).

Figure 2B:
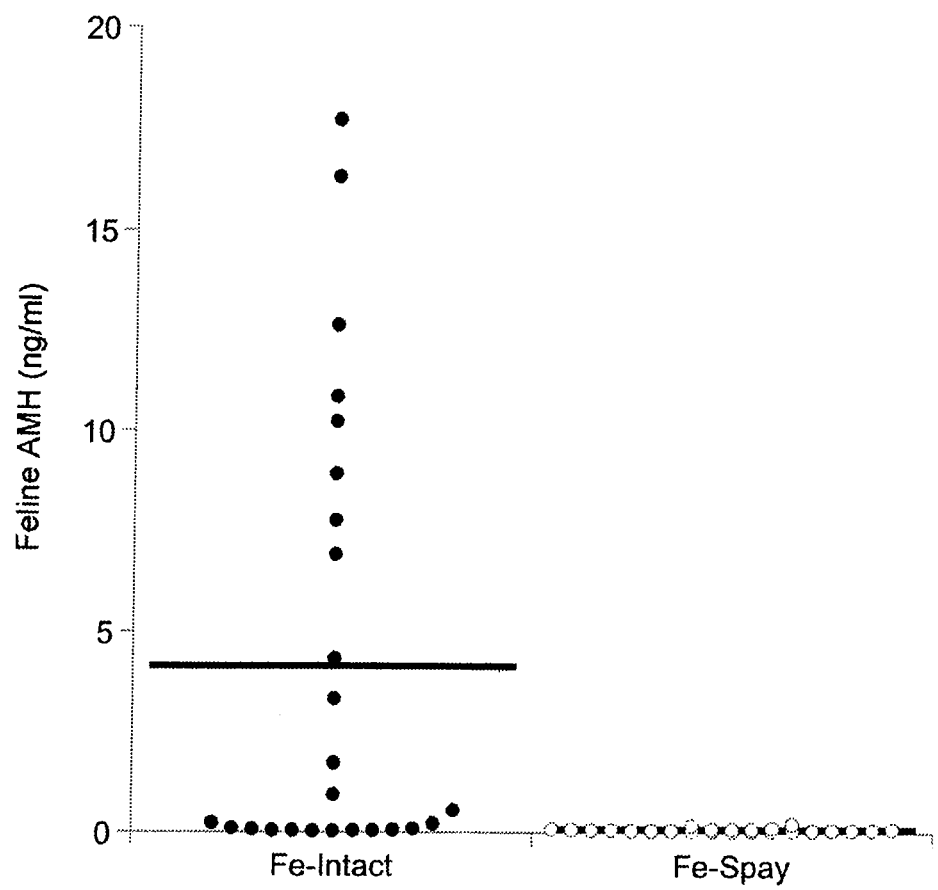

For cats, AMH concentration was uniformly low in the spay group (FIG. 2B). However, several cats in the intact group were also found to have low AMH levels. We suspect many of these privately owned cats may in fact have been spayed, especially the older individuals. The majority of the "intact" cats with low AMH were relatively older individuals (8 to 16 years), and some of them may have been reproductively senescent. Alternatively, their spay history may have been omitted from the lab requisition form, or they may in fact represent false negatives. These findings highlight the importance of developing and validating an assay with samples from dogs and cats that have had surgical documentation of their spay status.

Table 3 also presents data on the correlation of AMH levels with the state of being spayed (I=intact, S=Spayed, R=Remnant). As can be seen, there is a clear difference in detected AMH levels in spayed and intact animals, with the spayed animals having much lower detected levels of AMH than the intact animals. In comparing the AMH levels of dogs and cats within the intact groups, much lower concentrations were found in dogs than in cats. These results may indicate true differences in AMH levels in the two species, or the antibody used in the assay may have greater specificity for feline than for canine AMH.

TABLE 3

| ID | AMH | STATUS |
| --- | --- | --- |
| 1:1 | 0.41 | |
| 1:2 | 0.24 | |
| 1:4 | 0.14 | |
| 1:8 | 0.09 | |
| 1:16 | 0.07 | |
| 84871-07 I | 0.38 | I |
| 107881-07 I | 0.75 | I |
| 89679-07-3 I | 0.16 | I |
| 86253-07-6 I | 0.44 | I |
| 84871-07-7 I | 0.13 | I |
| 84779-07-2 I | 0.40 | I |
| 84871-07-5 I | 0.29 | I |
| 84871-07-3 I | 0.35 | I |
| 84871-07-2 I | 0.32 | I |
| 86253-07-4 I | 0.10 | I |
| 91132-07-1 I | 0.11 | I |
| 88811-07-2 neat I | 0.41 | I |
| 87366-07-2 I | 0.22 | I |
| 87366-07-4 I | 0.24 | I |
| 87366-07 I | 0.17 | I |
| 86253-07-5 I | 0.11 | I |
| 85657-07 S | 0.19 | R |
| 50377-08 OvR? | 0.18 | R |
| 106720-07 S | 0.06 | S |
| 108299-07 S | 0.36 | S |
| 106653-07 S | 0.07 | S |
| 108572-07 S | 0.05 | S |
| 104756-07 S | 0.06 | S |
| S. Cheraskin | 0.04 | S |
| 107358-07 S | 0.06 | S |
| 107848-07 S | 0.05 | S |
| 106254-07 S | 0.05 | S |
| 106577-07 S | 0.07 | S |
| 106758-07 (spun) S | 0.06 | S |
| 106961-07 S | 0.09 | S |
| 106231-07 S | 0.09 | S |
| 107869-07 S | 0.07 | S |
| 108592-07 S | 0.09 | S |

Example 3

Serum Anti-Müllerian Hormone

This example provides a demonstration of detectable levels of AMH in the serum of anestrous juveniles and adult hamsters. Siberian hamsters from our colony (14 hours of light per day, 14L) were transferred to LD (16L) or SD (10L) as breeding pairs to generate females for the following experiment. Experimental females were assigned to one of three groups (Table 4). The time of lights-off was synchronized for all animals to 1700 Eastern Standard Time (EST). Animals were originally derived from wild-bred stock obtained from Dr. K. Wynne-Edwards, Queen's University. Hamsters were weaned on postnatal day 18, ear-tagged for identification, weighed, and placed in polypropylene cages (2 to 4 siblings/cage). Food (Teklad 8626, Madison, Wis.) and water were available ad libitum. Ambient temperature and relative humidity were held constant between 21° C.±5 and 50±10%, respectively. Body mass, coat color, and vaginal patency were assessed and recorded weekly. Experimental procedures were approved by Cornell University's Institutional Animal Care and Use Committee and conducted in accordance with the NRC Guide for the Care and Use of Laboratory Animals.

TABLE 4

Group designations for experimental females

| Groups | Day lengths during 3-month age intervals | | | |
|---|---|---|---|---|
| | 0-3 mo | 3-6 mo | 6-9 mo | 9-12 mo |
| LD | 16L | 16L | 16L | 16L |
| LD-SD-LD | 16L[a] | 10L | 10L | 16L |
| SD-LD | 10L | 10L | 16L | 16L |

LD-Hamsters were held in 16L throughout. LD-SD-LD females were raised in 16L and transferred to 10L at 3 months of age, where they remained until 9 months of age, when they were transferred back to 16L. SD-LD females were raised in 10L and transferred to 16L at six months of age. Blood and tissue were collected from six animals from each group at 3, 6, 9, and 12 months of age.
[a]The photoperiodic histories of LD- and LD-SD-LD females were identical through 3 months of age, thus there were only two groups at this sampling age.

Five to eight animals from each group were killed at 3, 6, 9 and 12 months of age to collect blood and harvest reproductive tissues (details below). Females failing to respond to SD (maintained open vagina, summer pelage, and body mass) were excluded from the 3, 6, and 9-month-old cohorts. However, a sufficient number of photononresponders (NR) from within the LD-SD-LD group were available at the 12-month sampling point to include them as a fourth group. The essential study design was meant to determine if 6 months in SD results in a greater preservation of ovarian primordial follicles as compared to females held in LD, independent of the timing of the SD exposure relative to puberty.

AMH was measured in duplicate serum samples using an enzyme-linked immunosorbent assay (ELISA) produced by Diagnostic Systems Laboratories (Webster, Tex.). This ELISA was previously validated for the measurement of AMH in Siberian hamsters as described above. The intra- and inter-assay coefficients of variation were 22.0% and 19.8%, respectively. The minimum detection limit of the assay as reported by the manufacturer was 0.006 ng/ml.

Figure 3:
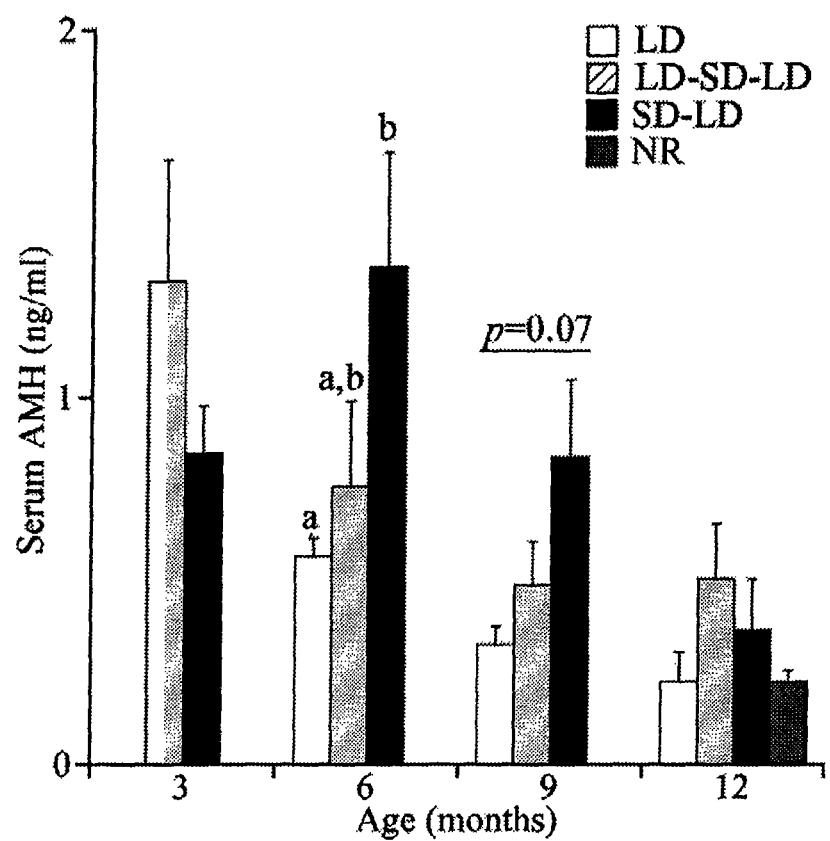
FIG. 3 provides a graph of mean (+SEM) serum AMH concentrations in female hamsters at 3, 6, 9, or 12 months of age. Sample sizes were five to eight animals in all groups. Each of the photoperiod-groups (LD, LD-SD-LD, and SD-LD) showed a significant change ($p<0.05$) in serum AMH concentration with age (refer to text for details), but between-group differences were limited to the 6-month-old cohort (no shared letters indicate significant differences).

Within the LD and SD-LD groups, serum AMH concentration varied significantly across age classes, but the patterns of variation were different. Serum AMH concentration declined significantly by 9 months of age in LD females, whereas AMH concentration in SD-LD females was not significantly changed until 12 months of age. For LD-SD-LD females, age-associated changes in serum AMH concentration approached significance (p=0.09), and the pattern suggests a slower decline as compared to the LD group (FIG. 3). Within each of the four age classes significant differences in serum AMH concentration were noted between photoperiod groups at 6 months of age and the values at 9 months of age approached significance (p=0.07).

Because serum AMH levels appear to be affected by differences in prevailing photoperiod (Kabithe and Place, 2008), exploring the relationship of serum AMH concentration to ovarian follicle counts was limited to 12 months of age. This was the only sampling time when all hamsters in all groups were held in the same photoperiod, i.e., LD (16L; see Table 1). The correlation of serum AMH concentration to the number of primordial follicles was modest, but significant ($r^2=0.17$, p=0.04). The correlation of AMH and follicle number was more substantial ($r^2=0.41$, p=0.0004) when the analysis was limited to the classes of follicles that represent the principal sources of AMH (primary+secondary follicles).

REFERENCES

Adam C L, Moar K M, Logie T J, Ross A W, Barrett P, Morgan P J & Mercer J G 2000 Photoperiod regulates growth, puberty and hypothalamic neuropeptide and receptor gene expression in female Siberian hamsters. Endocrinology 141 4349-4356.

Baarends W M, Uilenbroek J T, Kramer P, Hoogerbrugge J W, van Leeuwen E C, Themmen A P & Grootegoed J A 1995 Anti-Müllerian hormone and anti-müllerian hormone type II receptor messenger ribonucleic acid expression in rat ovaries during postnatal development, the estrous cycle, and gonadotropin-induced follicle growth. Endocrinology 136 4951-4962.

Balla A, Danilovich N, Yang Y & Sairam M R 2003 Dynamics of Ovarian Development in the FORKO immature mouse: structural and functional implications for ovarian reserve. Biology of Reproduction 69 1281-1293.

Bath L E, Wallace W H, Shaw M P, Fitzpatrick C & Anderson R A 2003 Depletion of ovarian reserve in young women after treatment for cancer in childhood: detection by anti-Müllerian hormone, inhibin B and ovarian ultrasound. Human Reproduction 18 2368-2374.

Crisosto N, Codner E, Maliqueo M, Echiburu B, Sanchez F, Cassorla F & Sir-Petermann T 2007 Anti-Mullerian hormone levels in peripubertal daughters of women with polycystic ovary syndrome Journal of Clinical Endocrinology and Metabolism 92 2739-43.

Dodge J C & Badura L L 2002 5HT and 5HIAA dialysate levels within the arcuate nucleus of the hypothalamus: relationship with photoperiod-driven differences in serum prolactin and luteinizing hormone in the Siberian hamster. Brain Research 946 171-178.

Durlinger A L, Kramer P, Karels B, de Jong F H, Uilenbroek J T, Grootegoed J A & Themmen A P 1999 Control of primordial follicle recruitment by anti-Müllerian hormone in the mouse ovary. Endocrinology 140 5789-5796.

Durlinger A L, Gruijters M J, Kramer P, Karels B, Kumar T R, Matzuk M M, Rose U M, de Jong F H, Uilenbroek J T, Grootegoed J A & Themmen A P 2001 Anti-Müllerian hormone attenuates the effects of FSH on follicle development in the mouse ovary. Endocrinology 142 4891-4899.

Durlinger A L, Gruijters M J, Kramer P, Karels B, Ingraham H A, Nachtigal M W, Uilenbroek J T, Grootegoed J A &

Themmen A P 2002a Anti-Müllerian hormone inhibits initiation of primordial follicle growth in the mouse ovary. Endocrinology 143 1076-1084.

Durlinger A L, Visser J A & Themmen A P 2002b Regulation of ovarian function: the role of anti-Müllerian hormone. Reproduction 124 601-609.

Ebling F J P 1994 Photoperiodic differences during development in the dwarf hamsters *Phodopus sungorus* and *Phodopus campbelli*. General and Comparative Endocrinology 95 475-482.

Elvin J A, Yan C, Wang P, Nishimori K & Matzuk M M 1999 Molecular characterization of the follicle defects in the growth differentiation factor 9-deficient ovary. Molecular Endocrinology 13 1018-1034.

Faddy M J & Gosden R G 1996 A model conforming the decline in follicle numbers to the age of menopause in women. Human Reproduction 11 1484-1486.

Fortune J E 2003 The early stages of follicular development: activation of primordial follicles and growth of preantral follicles. Animal Reproduction Science 78 135-163.

Hirobe S, He W W, Lee M M & Donahoe P K 1992 Müllerian inhibiting substance messenger ribonucleic acid expression in granulosa and Sertoli cells coincides with their mitotic activity. Endocrinology 131 854-862.

Hirshfield A N 1994 Relationship between the supply of primordial follicles and the onset of follicular growth in rats. Biology of Reproduction 50 421-428.

Hudson P L, Dougas I, Donahoe P K, Cate R L, Epstein J, Pepinsky R B & MacLaughlin D T 1990 An immunoassay to detect human mullerian inhibiting substance in males and females during normal development Journal of Clinical Endocrinology and Metabolism 70 16-22.

Ingraham H A, Hirokawa Y, Roberts L M, Mellon S H, McGee E, Nachtigal M W & Visser J A 2000 Autocrine and paracrine Müllerian inhibiting substance hormone signaling in reproduction. Recent Progress in Hormone Research 55 53-67.

Ikeda Y, Nagai A, Ikeda M A & Hayashi S 2002 Increased expression of Müllerian-inhibiting substance correlates with inhibition of follicular growth in the developing ovary of rats treated with E2 benzoate. Endocrinology 143 304-312.

Jost A 1947 Recherches sur la differenciation sexuelle de l'embryon de lapin. Archives d'anatomie microscopique et de morphologie experimentale 36 217-315.

Kenny H A, Bernard D J, Horton T H & Woodruff T K 2002a Photoperiod-dependent regulation of inhibin in Siberian hamsters: I. Ovarian inhibin production and secretion. Journal of Endocrinology 174 71-83.

Kenny H A, Bernard D J, Horton T H & Woodruff T K 2002b Photoperiod-dependent regulation of inhibin in Siberian hamsters: II. Regulation of inhibin production and secretion by pregnant mare serum gonadotropin. Journal of Endocrinology 174 85-94.

Kevenaar M E, Meerasahib M F, Kramer P, van de Lang-Born B M, de Jong F H, Groome N P, Themmen A P & Visser J A 2006 Serum AMH levels reflect the size of the primordial follicle pool in mice. Endocrinology 147 3228-3234.

Knight P G & Glister C 2006 TGF-beta superfamily members and ovarian follicle development. Reproduction 132 191-206.

Lee M M & Donahoe P K 1993 Mullerian inhibiting substance: a gonadal hormone with multiple functions Endocrine Reviews 14 152-64.

Liao j, Xu X & Wargovich M J 2000 Direct reprobing with anti-actin as an internal control for western blot analysis. Biotechniques 28 216-218.

Moffatt-Blue C S, Sury J J & Young K A 2006 Short photoperiod-induced ovarian regression is mediated by apoptosis in Siberian hamsters (*Phodopus sungorus*). Reproduction 131 771-782.

Pedersen T & Peters H 1968 Proposal for a classification of oocytes and follicles in the mouse ovary. Journal of Reproduction and Fertility 17 555-557.

Pellatt L, Hanna L, Brincat M, Galea R, Brain H, Whitehead S & Mason H 2007 Granulosa cell production of anti-Müllerian hormone is increased in polycystic ovaries. Journal of Clinical Endocrinology and Metabolism 92 240-255.

Place N J, Tuthill C R, Schoomer E E, Tramontin A D & Zucker I 2004 Short day lengths delay reproductive aging. Biology of Reproduction 71 987-992.

Scotti M A, Place N J & Demas G E 2007 Short-day increases in aggression are independent of circulating gonadal steroids in female Siberian hamsters (*Phodopus sungorus*). Hormones and Behavior 52 183-190.

Sir-Petermann T, Codner E, Maliqueo M, Echiburu B, Hitschfeld C, Crisosto N, Perez-Bravo F, Recabarren S E & Cassorla F 2006 Increased anti-Mullerian hormone serum concentrations in prepubertal daughters of women with polycystic ovary syndrome Journal of Clinical Endocrinology and Metabolism 91 3105-9.

Timonin M E, Place N J, Wanderi E & Wynne-Edwards K E 2006 *Phodopus campbelli* detect reduced photoperiod during development but, unlike *Phodopus sungorus*, retain functional reproductive physiology. Reproduction 132 661-670.

Tremblay J J & Viger R S 2001 GATA factors differentially activate multiple gonadal promoters through conserved GATA regulatory elements. Endocrinology 142 977-986.

Ueno S, Kuroda T, Maclaughlin D T, Ragin R, Manganaro T F & Donahoe P K 1989 Müllerian inhibiting substance in the adult rat ovary during various stages of the estrous cycle. Endocrinology 125 1060-1066.

van den Hurk R, Dijkstra G & De Jong F 2002 Enhanced serum oestrogen levels and highly steroidogenic, luteinized atretic follicles in the ovaries of the Djungarian hamster (*Phodopus sungorus*) kept under a short photoperiod from birth. European Journal of Endocrinology 147 701-710.

van Rooij I A, Broekmans F J, Scheffer G J, Looman C W, Habbema J D, de Jong F H, Fauser B J, Themmen A P & te Velde E R 2005 Serum antiMüllerian hormone levels best reflect the reproductive decline with age in normal women with proven fertility: a longitudinal study. Fertility and Sterility 83 979-987.

Visser J A, de Jong F H, Laven J S & Themmen A P 2006 Anti-Müllerian hormone: a new marker for ovarian function. Reproduction 131 1-9.

What is claimed is:
1. A method of assaying serum samples from a female cat or dog for the presence of Anti-Müllerian Hormone (AMH) comprising:
contacting a serum sample obtained from a female cat or dog that is not reproductively senescent and that has a non-postpartum anestrous period or interestrous of three months or greater with an antibody that binds to Anti-Müllerian Hormone (AMH) to form an antibody-Anti-Müllerian Hormone complex;

contacting said antibody-Anti-Müllerian Hormone complex with a labeled detection reagent to from a labeled detection reagent-antibody-Anti-Müllerian Hormone complex; and detecting the presence of said labeled detection reagent-antibody-Anti-Müllerian Hormone complex in an enzyme-linked immunosorbant assay or lateral flow assay.

2. The method of claim 1, further comprising quantifying the amount of AMH in said serum sample.

* * * * *